United States Patent [19]

Thompson et al.

[11] 4,357,943

[45] Nov. 9, 1982

[54] DEMAND CARDIAC PACEMAKER HAVING REDUCED POLARITY DISPARITY

[75] Inventors: David L. Thompson, Fridley; Jerome T. Hartlaub, New Brighton, both of Minn.; Marc T. Stein, Tempe, Ariz.

[73] Assignee: Medtronic, Inc., Minneapolis, Minn.

[21] Appl. No.: 225,679

[22] Filed: Jan. 16, 1981

Related U.S. Application Data

[63] Continuation of Ser. No. 957,814, Nov. 6, 1978, abandoned.

[51] Int. Cl.³ .............................................. A61N 1/36
[52] U.S. Cl. .............................................. 128/419 PG
[58] Field of Search ...................................... 128/419 P

[56] References Cited

U.S. PATENT DOCUMENTS 3,528,428  9/1970  Berkovits ................. 128/419 PG
3,949,759  4/1976  Brownlee et al. .......... 128/419 PG
4,275,737  6/1981  Thompson et al. ......... 128/419 PG Primary Examiner—William E. Kamm
Attorney, Agent, or Firm—Schroeder, Siegfried, Vidas, Steffey & Arrett

[57] ABSTRACT

A cardiac pacemaker of the type responsive to heart activity to affect the operation of the pacemaker. Detecting circuitry is provided having a differential input and an essentially polarity independent degree of response to sensed signals. A single polarity output signal is provided representative of sensed signals of either polarity. In a preferred embodiment, a differential input and differential output preamplifier is responsive to sensed signals to provide output signals of opposite polarity but like absolute value. An absolute value circuit responds to the opposite polarity signals to provide a single polarity output signal, the output signal being the same polarity without regard to the polarity of the sensed signals.

6 Claims, 3 Drawing Figures

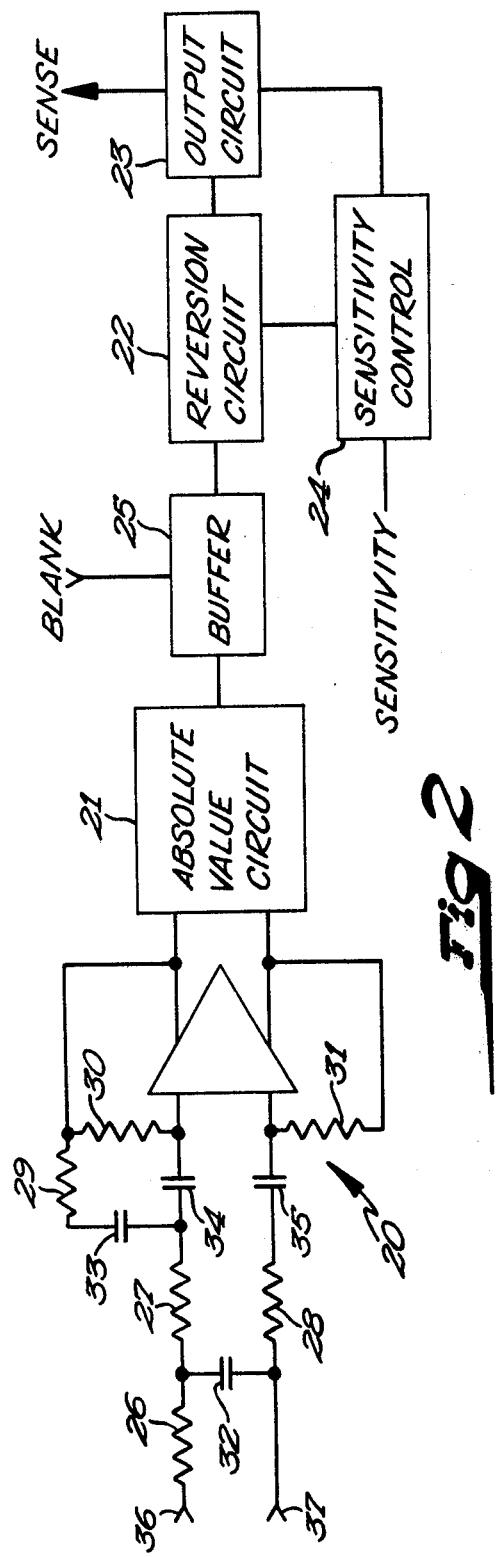

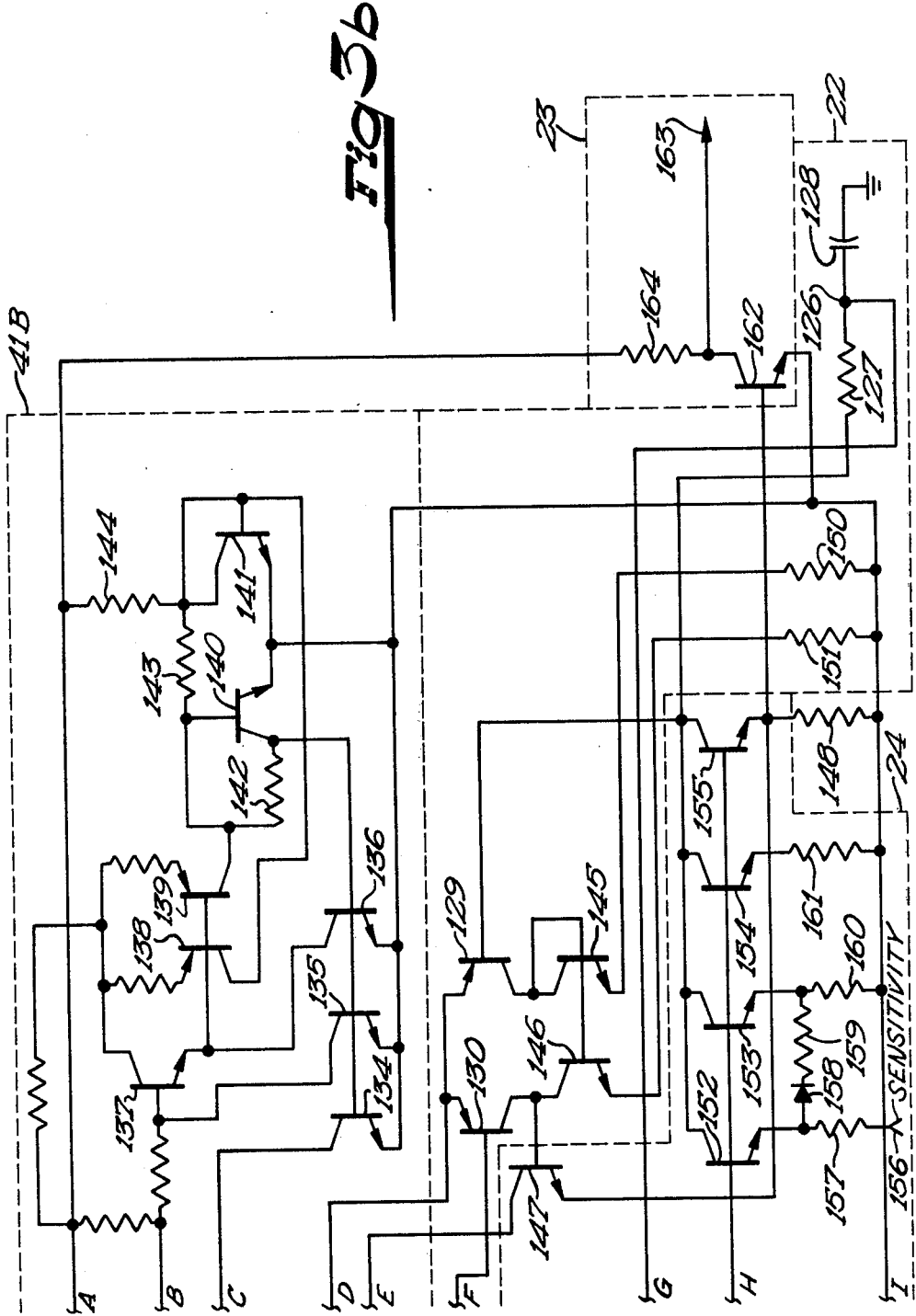

DEMAND CARDIAC PACEMAKER HAVING REDUCED POLARITY DISPARITY

This is a continuation of application Ser. No. 957,814, filed Nov. 6, 1978 now abandoned.

DESCRIPTION

Background of Prior Art

Body implantable cardiac stimulators or pacemakers are known to the prior art. An early pacemaker is disclosed by Greatbatch in U.S. Pat. No. 3,057,356, entitled "Medical Cardiac Pacemaker", which issued in 1962. This device included a relaxation oscillator that generated electrical pulses at a fixed rate. The pulses were applied to the heart to cause the heart to contract each time a pulse occurred.

Since 1962, the pacemaker has been continuously evolving. This evolution is outlined in concurrently filed co-pending application Ser. No. 957,962, filed in the name of David L. Thompson for Digital Cardiac Pacemaker, which is co-owned with the present invention and which is hereby incorporated by reference. As noted in the incorporated specification, pacing technology has lagged behind conventional state of the art electronic technology in its utilization of digital electronic circuits. One reason for this has been the high energy required to operate digital electronic circuits. Energy requirements are a major concern in pacemaker design. However, with the continuing advances of electronic technology, digital electronic circuits are increasingly feasible within the context of commercial pacemaker units.

The accuracy and reliability of digital electronic circuits are factors that encourage their use within the pacemaker context. The facility with which they can be programmed and reprogrammed to alter one or more operating parameters further enhances their utility. For example, pacemakers have been disclosed which respond to magnetic and/or radio frequency signals to alter an operating parameter. Pulse rate and pulse width may be programmed in this manner. In addition, pacemakers have been constructed which are inhibited in the presence of certain signals. A more detailed outline of prior art programmable pacemakers is contained in the incorporated specification. It should be noted that, as indicated in the incorporated specification, no known prior art pacemaker is capable of having more than two parameters, features or tests programmed on command.

The implementation of digital electronic circuitry within the pacemaker context provides the opportunity to program or reprogram one or several operating parameters, on command, via externally generated signals. For example, pulse rate, pulse width and pulse amplitude can be externally established at one of any number of combinations. In addition, the refractory period may be established and altered. Further, digital circuitry can be programmed on a temporary or permanent basis, as desired. Of course, other operating parameters or characteristics can also be externally programmable.

Clearly then, a pacemaker utilizing digital electronic circuitry would have a more universal application by allowing the pacemaker to be programmed to fit the needs of a particular application as opposed to being manufactured for limited applications. In addition, such a unit can be instructed to give an external indication of its program status, particularly in instances where that status is not directly observable. However, even with the implementation of digital circuitry, certain analog circuitry is necessary to generate and/or transmit various control signals and to respond to the digital circuitry to effect its programming.

BRIEF SUMMARY OF THE INVENTION

The present invention provides analog circuitry intended for cooperation with the digital circuitry disclosed in the incorporated specification to assist in the performance of the pacemaking function. Among the analog circuit functions necessary within the context of the digital circuitry of the incorporated specification, are the demodulation of the programming signal, a detection of heart activity during operation in a demand mode and provision of clock pulses. Additionally, analog circuitry is employed to give an indication of battery status and to impose an upper rate limit on the stimuation initiating signals generated by the digital circuit. The digital circuitry of the incorporated specification provides a signal to control the sensitivity of the sense amplifier and a signal to establish a refractory period within the sense amplifier. The output analog circuit is controlled by the digital circuit to speed up the recharging of a capacitor in the output circuit, to establish the magnitude of the output pulses and to impose an upper rate limit on the output stimulation pulses. As detailed in the incorporated specification, one of the clock pulse generators is enabled by a signal from the digital circuit.

Within the context of cooperating analog and digital circuitry for the generation and application of stimulating pulses, the present invention is directed to a sense amplifier having an output indicative of the detection of heart activity, the sense amplifier being responsive to input signals to establish its sensitivity and a refractory period. The sense amplifier includes a preamplifier having a degree of response essentially independent of the polarity of signals applied to its input. An absolute value circuit responds to the output of the preamplifier to provide a single polarity output signal representative of signals of either polarity appearing at the input of the preamplifier. Thus, the polarity disparity attending prior art sense amplifiers is largely overcome as a result of the essentially polarity independent response of the preamplifier and the single polarity output of the absolute value circuit. A reversion circuit detects a signal resulting from sensed heart activity in the output of the absolute value circuit, that detection resulting in the provision of an output signal from an output circuit. A sensitivity control is provided to cooperate with the reversion circuit to alter its sensitivity to signals appearing at the output of the absolute value circuit while a buffer is provided between the absolute value circuit and the reversion circuit and is controlled to regulate the transmission of signals between the absolute value circuit and the reversion circuit. The period during which signals are blocked from the reversion circuit is referred to herein as a refractory period. The output circuit includes a system for altering the sensitivity of the reversion circuit during an output signal to enhance the response of the reversion circuit to a signal resulting from natural heart activity.

In a preferred embodiment, the preamplifier has a differential input and a differential output, the output signals being of like absolute value but of opposite polarity. The absolute value circuit responds to the positive output signal from the preamplifier to provide an output of a single plurality without regard to the polarity of the signals appearing at the input of the preamplifier. Thus, there is provided a versatile sense amplifier which greatly reduces polarity disparity and which has a programmable sensitivity and an externally established refractory period.

BRIEF DESCRIPTION OF THE DRAWINGS

FIG. 2 illustrates the operation of a sense amplifier forming a part of the analog circuitry of FIG. 1.

FIGS. 3a and 3b illustrate in more detail the sense amplifier of FIG. 2.

DETAILED DESCRIPTION OF THE INVENTION

Figure 1:
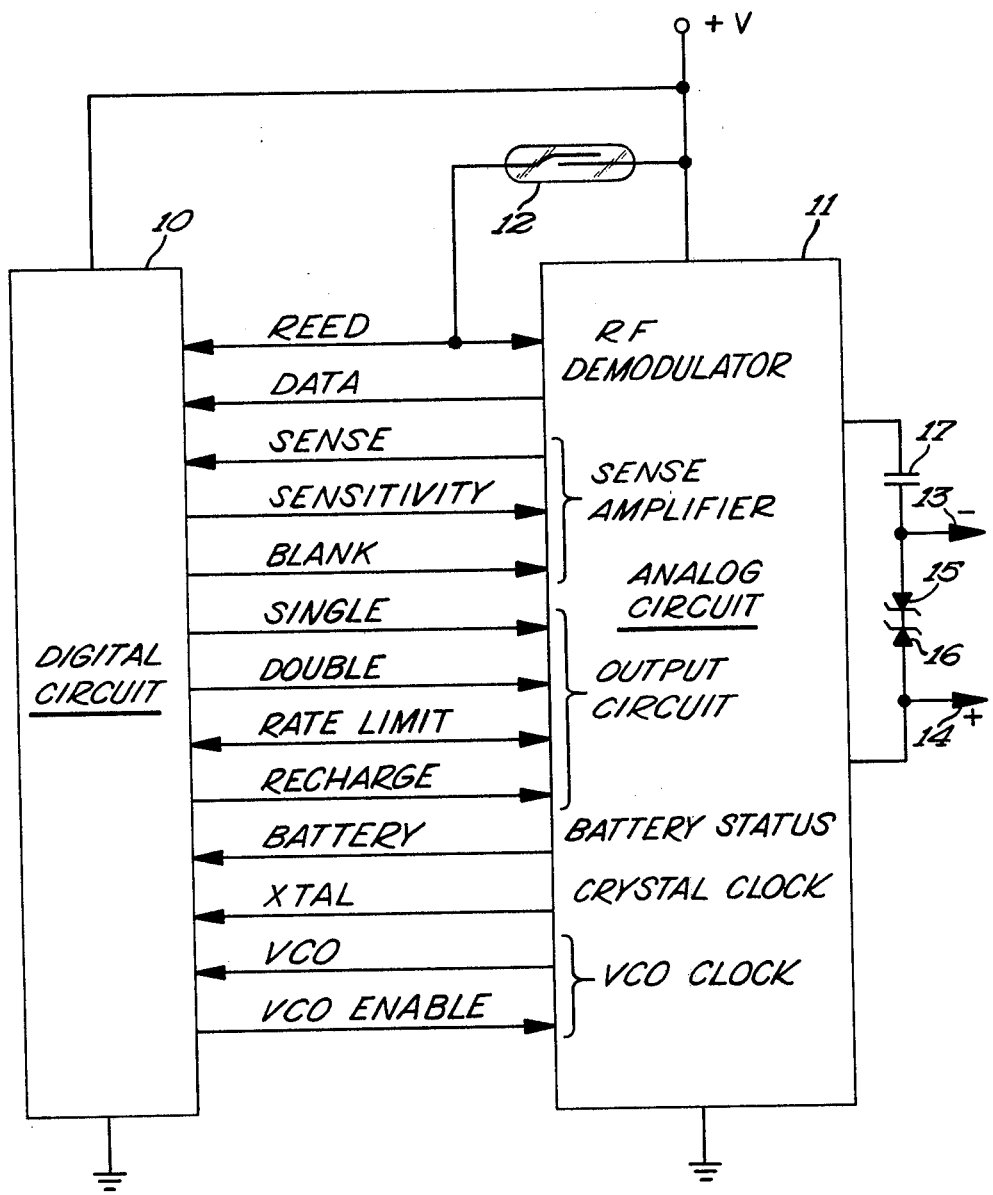
FIG. 1 shows the interconnection and cooperation between the digital circuit of the incorporated specification and a cooperating analog circuit of which the present invention is a part.

Referring now to FIG. 1 there is shown a block diagram illustrating the interconnections between Digital Circuitry 10 (as disclosed in the incorporated specification) and Analog Circuitry 11 (of which the present invention is a part). Both the Digital Circuit 10 and Analog Circuit 11 are connected between a source of positive potential +V and a reference potential, such as ground. The source of positive potential may be a battery such as the conventional lithium diode battery which generates approximately 2.8 volts.

The Analog Circuit 11 consists of various distinct electrical systems which may be referred to functionally as an RF Demodulator, a Sense Amplifier, an Output Circuit, a Battery Monitor and Status Indicator, a Crystal Clock and a Voltage Controlled Oscillator Clock. The Digital Circuit 10 includes all of the digital logic necessary to cause a programming change, memory to store the digital code manifesting the desired values for the program parameters and digital timing means for causing a stimulation pulse to be generated in the programmed manner. The signals applied between the Digital Circuit 10 and Analog Circuit 11 are REED, DATA, SENSE, SENSITIVITY, BLANK, SINGLE, DOUBLE, RATE LIMIT, RECHARGE, BATTERY, XTAL, VCO and VCO ENABLE.

A magnetically actuated reed relay switch 12 is connected between the source of positive potential +V and both the Digital Circuit 10 and the RF Demodulator of Analog Circuit 1. Reed switch 12 is normally open and is closed as by placing a magnet in close proximity thereto. When closed, a +V, or logic "1", REED signal is applied to both the Digital Circuit 10 and Analog Circuit 11. On removal of the magnet, the reed switch 12 opens and a ground, or logic "0", signal is applied to the Digital Circuit 10 and Analog Circuit 11. The RF Demodulator is enabled by a +V REED signal produced by a closing of the reed switch 12 to provide a DATA signal to the digital circuit 10. The DATA signal (the Digital Circuit 10 programming signal) is a pulse signal going from logic "0" to logic "1", as described in the incorporated specification, which is representative of pulse bursts generated externally.

The Sense Amplifier portion of the analog circuit 11 provides a SENSE signal each time natural heart activity is detected to restart the timing cycle of the Digital Circuit 10, when operating in a demand mode. A SENSITIVITY signal is provided by the Digital Circuit 10 in accordance with its programming to establish the detection level of the Sense Amplifier. A BLANK signal is generated by the Digital Circuit 10 and applied to the Sense Amplifier portion of the Analog Circuit 11 to establish the refractory period of the Sense Amplifier and to allow the components within the Sense Amplifier to reset themselves.

The Output Circuit of analog circuit 11 includes output terminals 13 and 14 which are adapted for connection to a conventional lead, in a known manner. The output terminal 14 may be connected to a metal casing housing the pacemaker unit or a plate forming a part of the casing in a unipolar lead system or it may be connected to a second lead in a bipolar lead system, depending on the type of lead system employed. Output terminal 13 is coupled through a capacitor 14 to the analog Output Circuit and to the heart (not shown). In addition, a pair of Zener diodes 15 and 16 have their anodes coupled together and their cathodes coupled to output terminals 13 and 14, respectively. Diodes 15 and 16 function in a conventional manner to prevent damage to the pacemaker circuitry in the presence of large extraneous signals such as are caused by electrocautery. The Output Circuit of Analog Circuit 11 includes elements responsive to a SINGLE or DOUBLE signal from Digital Circuit 10 to control the amplitude of output signals applied across output terminals 13 and 14. A RECHARGE signal from Digital Circuit 10 speeds up the recharging of output capacitor 14 while the Output Circuit of Analog Circuit 11 provides a RATE LIMIT signal to Digital Circuit 10 to provide an upper limit to the rate at which stimulation initiating signals are generated. Digital circuit 10 also provides a RATE LIMIT signal to the Output Circuit of Analog Circuit 11 to provide an upper limit to the rate at which stimulation pulses may be applied by the Output Circuit.

In addition to the above, Analog Circuit 11 includes circuitry which monitors the status of the battery to provide an indication of that status in the form of the signal BATTERY. Also, clock pulses are provided to the Digital Circuit 10 in the form of signals XTAL and VCO. Within the context of the Digital Circuit of the incorporated specification, the XTAL signal is a generally square wave pulse signal occurring at a frequency of 32,768 Hz and the VCO signal is a square wave pulse signal having a preset frequency of whenever +V is equal to 2.8 volts. As +V decreases with time, as the battery depletes, the frequency of the VCO signal will also decrease, in known manner. The VCO signal is used in the timing circuitry of Digital Circuit 10 to establish the exact width of stimulating pulse. In order to maintain a constant energy of this pulse, it is necessary that the pulse increase in width as +V decreases. The VCO clock pulse generator is enabled only during the time the stimulating pulse is to be provided and is enabled by the signal VCO ENABLE.

Referring now to FIG. 2, there is shown a block diagram of a Sense Amplifier forming a portion of the Analog Circuit 11 of FIG. 1. The Sense Amplifier includes a preamplifier section indicated generally at 20, an Absolute Value Circuit 21, a Reversion Circuit 22, an Output Circuit 23 and a Sensitivity Control 24. A Buffer 25 is provided intermediate the Absolute Value Circuit 21 and Reversion Circuit 22 to prevent loading on the Absolute Value circuit from the Reversion Circuit. Buffer 25 is responsive to the BLANK signal from Digital Circuit 10 to turn off and block signals from the Reversion Circuit 22.

Preamplifier 20 is a differential input, differential output device having a dual feedback active filter formed of resistors 26-31 and capacitors 32-35. It is designed to have an open loop gain of approximately 60,000 with a unity gain crossover point of approximately 2 kHz. The dual negative feedback method minimizes the number of external components used. As will be described more fully below, the differential input of the preamplifier 20 allows an essentially polarity independent degree of response to signals appearing at the input terminals 36 and 37. That is, preamplifier 20 is essentially identically responsive to signals appearing at the terminals 36 and 37 without regard to polarity. The differential output of preamplifier 20 provides two signals of opposite polarity but of essentially the same absolute value, each being representative of signals appearing at the inputs 36 and 37.

The Absolute Value Circuit 21 responds to the differential output signals of preamplifier 20 to provide a single polarity signal representative of the signal sensed at the inputs 36 and 37. Thus, preamplifier 20 and Absolute Value Circuit 21 combine to provide signals of a single polarity representative of signals appearing at the terminals 36 and 37, but without regard to the polarity of the signals at the terminals 36 and 37. In this way, the detecting circuitry contained within Reversion Circuit 22 need be responsive to signals of but a single polarity without thereby creating a polarity disparity within the Sense Amplifier illustrated in FIG. 2. The sensitivity of the Reversion Circuit 22 to the output of the Absolute Value Circuit 21 is controlled by Sensitivity Control 24, the sensitivity being established by the SENSITIVITY signal from the Digital Circuitry of the incorporated specification causing its timing cycle to be restarted in a known manner. The line between Output Circuit 23 and sensitivity control represents a sensitivity hysteresis function which will be explained more fully below.

Figure 3A:
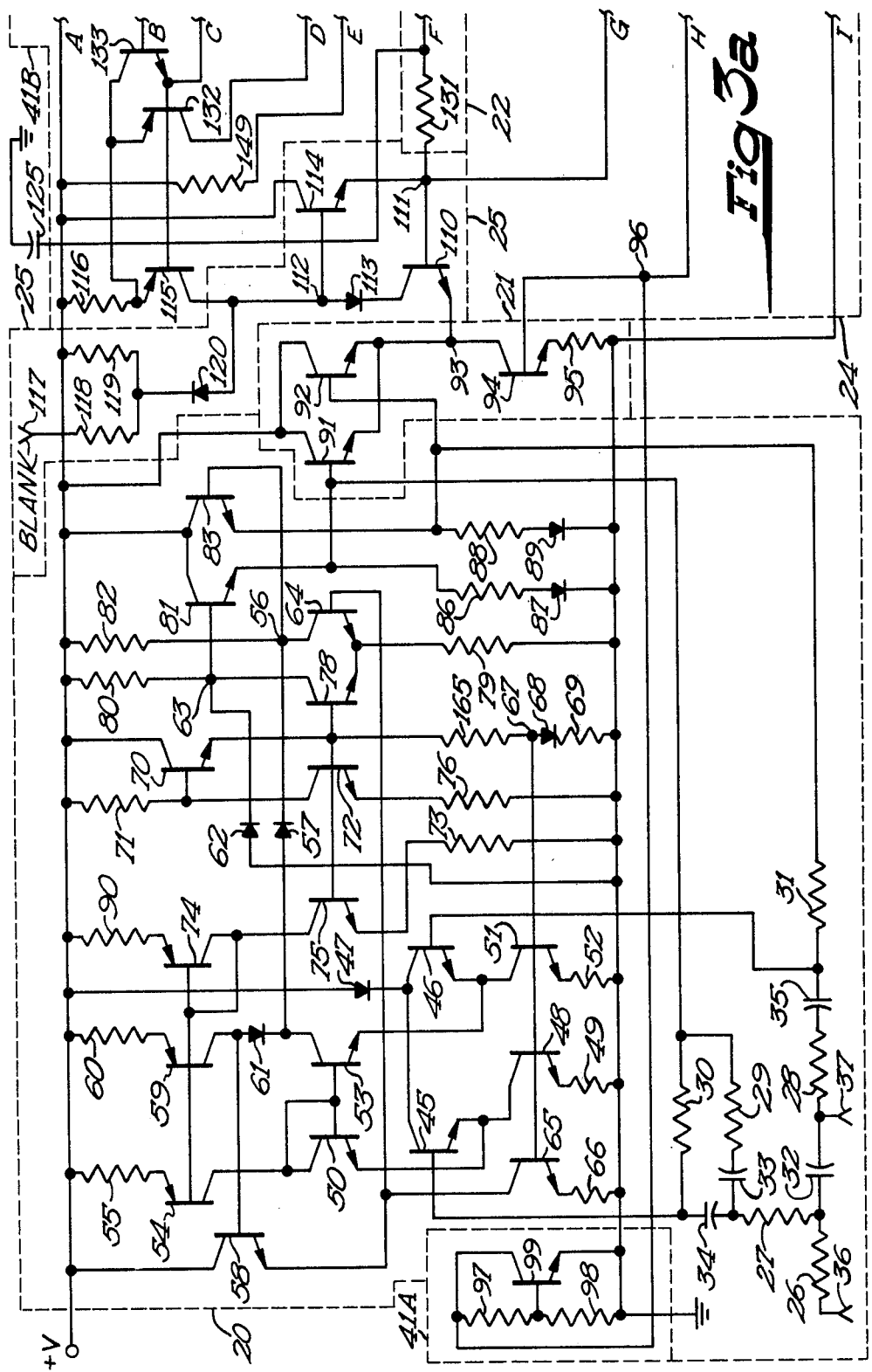

Referring now to FIG. 3 there is illustrated in separate FIGS. 3a and 3b a preferred embodiment of the Sense Amplifier of FIG. 2 with functional elements 20-25 being set out in boxes of like reference numeral formed of broken lines. Elements forming the dual feedback filter illustrated in FIG. 2 are illustrated with like reference numeral in FIG. 3. Boxes 41A and 41B contain elements which set up supply-independent voltage references and bias currents as is described more fully below. Connecting lines A to I in FIG. 3a are intended for connection to the line of like reference character in FIG. 3b.

Signals apppearing at the input terminals 36 and 37 are applied through the active filter, to the bases of transistors 45 and 46. Transistors 45 and 46 form the input differential pair having their collectors connected to +V through diode 47. The emitter of transistor 45 is connected to a current sink formed of transistor 48 and resistor 49 and to the emitter of a transistor 50. Similarly, the emitter of transistor 46 is connected to a current sink formed of transistor 51 and resistor 52 and to the emitter of transistor 53. The bases of transistors 50 and 53 and the collector of transistor 50 are connected to a current source formed of transistor 54 and 55. The collector of transistor 53 is connected to a junction 56 via capacitor 57 and, via a diode 61, to the base of transistor 58 and a current source formed of transistor 59 and resistor 60. A capacitor 62 connects a junction 63 to ground.

The emitter of transistor 58 is connected to the base of a transistor 64 and to a current sink formed of transistor 65 and resistor 66. The bases of transistors 48, 51 and 65 are connected to a junction 67, the junction 67 being connected to ground via diode 68 and resistor 69 and to a junction 77 via resistor 165. A transistor 70 has its emitter connected to the junction 77, its collector connected to +V while its base is connected to +V via resistor 71 and to the collector of a transistor 72. The emitter of transistor 72 is connected to ground via resistor 73. The base of transistor 59 is connected to the base of transistor 54, the collector and base of a transistor 74 and the collector of a transistor 75. The emitter of transistor 75 is connected to ground via a resistor 76 and the base of transistor 75, and the base of transistor 72, are connected to the junction 77. Junction 77 is connected to the junction 67 via resistor 165 and the base of a transistor 78, transistor 78 having its emitter connected to the emitter of transistor 64 and to ground via resistor 79. The collectors of transistors 64 and 78 are connected to junctions 56 and 63, respectively. Junction 63 is connected to +V via resistor 80 and to the base of a transistor 81. Similarly, junction 56 is connected to +V via resistor 82 and to the base of a transistor 83. The collectors of transistors 81 and 83 are connected to +V while their emitters are connected to junctions 84 and 85, respectively. Junctions 84 and 85 serve as the output terminals for preamplifier 20 with junction 84 being connected to ground via resistor 86 and diode 87 and junction 85 being connected to ground via resistor 88 and diode 89.

As stated above, transistors 45 and 46 constitute the input differential pair. Diode 47 prevents basecollector current to +V in transistor 46 during a stimulation pulse while diode 61 increases the dynamic range of the input differential pair during supply voltage depletion. Transistors 70 and 72, in conjunction with resistors 71 and 73, set up a one-half +V stable reference at the junction 77. Diode 68 and resistors 69 and 165 set up a tail current for transistors 45 and 46 via the current sinks formed in part by transistors 48 and 51 as well as for transistor 58 via the current sink formed in part by transistor 65.

Transistor 58 is an emitter follower which couples the signal from the input differential pair to the transistors 64 and 78 which form the second gain stage in the amplifier. The signals appearing at the junctions 56 and 63 are of opposite polarity having an absolute amplitude value representative of signals appearing across the terminals 36 and 37. The transistors 81 and 83 are emitter followers which drive the Absolute Value Circuit 21. The source current for the input differential pair are set up by transistors 54, 57, 74 and 75 and resistors 55, 60, 76 and 90. Capacitors 57 and 62 set the high frequency rolloff of the preamplifier while diode 87 and resistor 86 and diode 89 and resistor 88 set up a tail current from the emitter followers formed of transistors 81 and 83, respectively.

Preamplifier 20 has a degree of response essentially independent the polarity of the signals appearing at the terminals 36 and 37. It has a differential input and a differential output, the signals appearing at the output being of opposite polarity with the absolute value of the signals appearing at the terminals 36 and 37. In this manner, the polarity disparity attending prior art sense amplifiers is greatly reduced and the Sense Amplifier can reliably respond to sensed signals representative of heart activity of either polarity.

The junction 84 is connected to the base of a transistor 91 while the junction 85 is connected to the base of a transistor 92. The bases of transistors 91 and 92 are also connected to resistors 30 and 31, respectively, resistors 30 and 31 being the negative feedback resistors associated with the active filter. The collectors of transistors 91 and 92 are connected to +V while their emitters are connected to a junction 93. The junction 93 comprises the output terminal of the Absolute Value Circuit 21 and is connected to the collector of a transistor 94. The emitter of transistor 94 is connected to ground via resistor 95 and its base is connected to a junction 96. Resistors 97 and 98 and transistor 99 in box 41A set up a reference voltage which is applied to the base of transistor 94 as well as to transistors forming a portion of the Sensitivity Control 24, as will be described below.

Transistors 91 and 92 are emitter followers. Accordingly, the signal appearing at the junction 93 will approximate the most positive signal appearing at the bases of transistors 91 and 92. Inasmuch as the signals appearing at the junctions 84 and 85 are of opposite polarity the positive one of those signals will result in a positive signal at the junction 93. Accordingly, a positive signal appears at the junction 93 which is representative of signals appearing at the terminals 36 and 37 without regard to polarity. That is, signals of either polarity appearing at terminals 36 and 37 will result in a single polarity signal (in this case positive) at junction 93, that signal being representative of the signal at the terminals 36 and 37.

The signal appearing at junction 93 is applied as an input to a unity gain amplifier 25. The amplifier 25 functions as a buffer between the Absolute Value Circuit 21 and the Reversion Circuit 22. The junction 93 is connected to the emitter of a transistor 110. The base of transistor 110 is connected to a junction 111 while the collector of transistor 110 is connected to a junction 112 via diode 113. The junction 112 is connected to a transistor 114 and to a current source formed of transistor 115 and resistor 116. As described to this point, the devices 110, 113, and 114 establish a unity gain Buffer between the absolute value circuit 21 and the reversion circuit 22.

A blanking circuit in the form of a terminal 117, resistor 118, resistor 119 and diode 120 are interconnected with the Buffer 25 to provide a refractory period during which the Reversion Circuit 22 resets itself and to prevent a charging of the Reversion Circuit capacitor during and after stimulation pulses. When a BLANK signal, a logic "0" signal, is applied to the terminal 117, the unity gain Buffer circuitry is turned off for the duration of the BLANK signal, 100 milliseconds, for example.

Junction 111 serves as the input to Reversion Circuit 22, the Reversion Circuit 22 including the capacitor 25 as well as the components within the box 22. As is well known in the art, there is an offset between junctions 93 and 111 such that the signal appearing at the junction 111 is slightly less than the signal appearing at the junction 93 but is otherwise identical to it. The signal appearing at junction 111 is applied to a junction 126 between the resistor 127 and a capacitor 128. Capacitor 128 is connected to ground while resistor 127 is connected to the base of a transistor 129. Junction 111 is also connected to the base of a transistor 130 and to capacitor 125 via resistor 131. Capacitor 125 is connected to ground.

The emitters of transistors 129 and 130 are connected to the collector of a transistor 132. Transistor 115 and transistors 132–141, together with their associcated resistors within box 41B, set up a supply-independent voltage reference for a Battery Monitor Circuit (not shown) forming a part of the Analog Circuit 11 of FIG. 1 and set up bias currents for the unity gain Buffer 25 and Reversion Circuit 22. For example, transistors 134–136 are 2.72 area scaled transistors which, in conjunction with transistor 140 and a resistor 142 set up current in their respective collectors. Transistor 141 together with resistors 143, 144 provide a current for startup when power is first applied. Transistors 133 and 137 minimize effects on currents at low battery conditions.

The collector of transistor 129 is connected to the collector and base of a transistor 145 while the collector of transistor 130 is connected to the collector of a transistor 146 and to the base of a transistor 147. The emitter of transistor 147 is connected to ground via resistor 148 and to the base of a transistor 162 while its collector is connected to +V via resistor 149. Transistors 145 and 146 form current sinks in conjunction with resistors 150 and 151, respectively.

Transistor 147 and resistors 148 and 149 provide a sensitivity hysteresis function in a manner to be described more fully below. In addition, Reversion Circuit 22 works in conjunction with Sensitivity Control Circuit 24 and the Output Circuit 23. Transistors 152–155 of Sensitivity Control Circuit 24 have their collectors connected to the base of transistor 129 and their bases connected to junction 96. The emitter of transistor 152 is connected to a terminal 156 via resistor 157 and to the emitter of transistor 153 via diode 158 and resistor 159. The terminal 156 receives the SENSITIVITY signal from the Digital Circuit of the incorporated specification. The emitter of transistor 153 is connected to ground via resistor 160 while a resistor 161 connects the emitter of transistor 154 to ground. The emitter of transistor 155 is connected to resistor 148, to the emitter of transistor 147 and to the base of transistor 162. Transistor 162 controls the output signal and has its collector connected to a terminal 163 and to +V via resistor 164 while its emitter is connected to ground. The SENSE signal is provided to the Digital Circuitry of the incorporated specification at terminal 163.

As will become apparent from the following discussion, when no signal is applied to terminal 156, an intermediate sensitivity is selected for the Reversion Circuit 22. When the terminal 156 is connected to a positive potential via the Digital Circuitry 10, the Reversion Circuit 22 is in its most sensitive state. Conversely, when the terminal 156 is connected to ground via the Digital Circuitry 10, Reversion Circuit 22 is in its least sensitive state. Assuming for the moment, that Sensitivity Control Circuit 24 is in the intermediate setting (i.e. no signal appearing at terminal 156) each of the current sinks including transistors 153–155 are operative and establish a voltage drop across resistor 127 resulting in a turnoff of transistor 130 and a turnon of transistor 129. This is the quiescent reversion Circuit condition. When a signal is applied to the junction 111 the base of transistor 129 rises more rapidly than the base of transistor 130 because of the time constant associated with resistor 131 and capacitor 125. If the input is of sufficient amplitude to overcome the bias on transistors 129 and 130 established by the voltage drop across resistor 127, transistor 130 turns on and transistor 129 turns off. The turn on of transistor 130 turns on transistor 147 and thus transistor 162. The turn on of transistor 162 results in a signal at terminal 163 of ground potential—a logic "0" SENSE signal in the context of digital circuit 10 of FIG. 1—indicating the detection of heart activity.

When the terminal 156 is connected to a positive potential, the current associated with the current sink including transistor 153 is disabled and thus a lesser current is flowing through resistor 127 establishing less of a bias on the base of transistor 129. Thus, Reversion Circuit 22 has a greater sensitivity. Conversely, when terminal 156 is connected to ground, the current sink including transistor 152 is enabled increasing the current flow through resistor 127 and the bias on transistor 129. In this condition, the Reversion Circuit 22 is in its least sensitive setting.

Reversion Circuit 22 functions as an interference discriminator in a manner similar to the circuit disclosed in U.S. Pat. No. 3,927,677, issued Dec. 23, 1975 for DEMAND CARDIAC PACER, which is co-owned with the present invention and which is hereby incorporated by reference. Within the context of the present invention, a continuous wave signal results in a charging of capacitor 125 of a reference level (an average value determined by the time constant of capacitor 125 and resistor 131 and the repetition rate of the incoming signal). In a non-repetitive signal (such as an R wave) occurs during this continuous wave signal, it will result in a charge of capacitor 125 to a second level (a peak riding above the average DC level) allowing transistor 129 to respond to it and turn off (dependent, of course, on the magnitude of the signal and sensitivity of the Reversion Circuit 22). Thus, the Reversion Circuit 22 responds differentially to signals representative of extraneous repetitive noise and sensed heart activity to result in a digital circuit compatible output signal (SENSE), even in the presence of repetitive noise, while its sensitivity may be programmed in accordance with the state of the digital circuitry. During the BLANK signal, the Reversion Circuit 22 resets itself by assuming the quiescent condition—transistor 129 "on" and transistor 130 "off".

Transistor 147 and resistors 148 and 149 perform a sensitivity hysteresis function to enhance the provision of an output signal. As an output pulse is initiated, the junction between the emitter of transistor 147 and resistor 148 rises in voltage which turns off transistor 155. This decreases the current flow through the resistor 127. Thus, a positive feedback is initiated in that as transistor 129 is turned off by a positive signal coming from the unity gain Buffer 25, an output is initiated and the current through the resistor 127 is lowered resulting in an increase in the base voltage of transistor 129 turning it off even faster. When the output transistor 162 begins to turn off, the voltage at the junction of the emitter of transistor 147 and resistor 148 drops toward ground initiating the flow of current through transistor 155 and increasing the current flow through resistor 127 speeding up the turn on of transistor 129 and, thus, the turnoff of transistor 130.

The essentially polarity independent response of the preamplifier 20 and Absolute Value Circuit 21 for the purpose of reducing polarity disparity are enhanced by the fact that the current sources and sinks have their emitters "degenerated" by resistors which stabilizes them to make them more nearly matching for polarity disparity. However, other techniques may be employed without departing from the scope of the invention. In addition, at least the input differential pair formed of transistors 45 and 46 and the Absolute Value Circuit transistors 91 and 92 are preferably "matched" by placing them in close proximity and providing them with the same geometry and connections, again for polarity disparity. This is preferable with the feedback resistors 30 and 31 as well. In a preferred embodiment, the transistor 129 can be an area scaled device which, together with the selection of the resistances of resistors 150 and 151 can provide an offset corresponding to the offset between the junctions 93 and 111. The use of current sources or sinks stabilizes the currents over the voltage ranges of interest. However, the present invention may be implemented in manners other than those stated as preferable. Accordingly, it is to be understood that, within the scope of the appended claims, the invention may be practiced otherwise than as specifically described.

We claim:

1. In a cardiac pacemaker of the type having means for sensing heart activity, means responsive to the sensing means for detecting heart activity and means responsive to the detecting means for affecting the operation of said pacemaker, the improvement wherein said detecting means comprises:

amplifier means responsive to said sensing means and having differential input means and dual output means and an essentially polarity independent degree of response to said sensing means, the signals appearing at said dual output means being of opposite polarity to each other and having an absolute value representative of signals appearing at said input means; and absolute value means connected to receive both amplifier output means opposite polarity signals for providing single polarity signals representative of signals of either polarity sensed by said sensing means.

2. The pacemaker of claim 1 wherein said first and second means each comprise responsive to signals of a single polarity.

3. The pacemaker of claim 1 wherein said first and second means are responsive to signals of the same polarity.

4. The pacemaker of claim 3 wherein the outputs of said first and second means are summed.

5. The pacemaker of claim 3 wherein said first and second means comprise emitter follower means having common emitter and common collector connections.

6. The pacemaker of claim 1 wherein said absolute value means comprises first and second input means each responsive to a different one of said dual output means signals.

* * * * *